United States Patent [19]
Clague et al.

[11] Patent Number: 5,971,023
[45] Date of Patent: Oct. 26, 1999

[54] JUNCTION FOR SHEAR SENSITIVE BIOLOGICAL FLUID PATHS

[75] Inventors: Cynthia T. Clague; Frank D. Dorman, both of Minneapolis; Robert C. Hamlen, St. Paul; Donald W. Hegeman, III, Shakopee; Timothy A. Miller, Eagan, all of Minn.; Joseph E. Poissant, Brandenton, Fla.; Richard T. Stone, Minneapolis; Michael P. Sullivan, Deephaven, both of Minn.

[73] Assignee: Medtronic, Inc., Minneapolis, Minn.

[21] Appl. No.: 08/800,904

[22] Filed: Feb. 12, 1997

[51] Int. Cl.$^6$ ........................... F15C 1/16
[52] U.S. Cl. ............ 137/813; 137/811; 137/812
[58] Field of Search ........................ 137/808, 809, 137/810, 811, 812, 813

[56] References Cited

U.S. PATENT DOCUMENTS

| | | | |
|---|---|---|---|
| 3,461,897 | 8/1969 | Kwok | 137/809 |
| 3,864,055 | 2/1975 | Kletschka et al. | 415/1 |
| 3,957,389 | 5/1976 | Rafferty et al. | 415/1 |
| 4,213,752 | 7/1980 | Henshaw | 417/206 |
| 4,259,988 | 4/1981 | Singh | 137/812 |
| 4,403,911 | 9/1983 | Possell | 415/90 |
| 4,585,435 | 4/1986 | Vaillancourt | 604/27 |
| 4,917,571 | 4/1990 | Hyll et al. | 415/206 |
| 5,080,137 | 1/1992 | Adams | 137/810 |
| 5,127,800 | 7/1992 | Hyll et al. | 415/203 |

FOREIGN PATENT DOCUMENTS

| | | | |
|---|---|---|---|
| 0 421 280 A1 | 9/1990 | European Pat. Off. | F04D 11/00 |
| 1 503 469 | 10/1976 | United Kingdom | A61M 25/00 |
| 2138504 A | 10/1984 | United Kingdom | F04D 29/44 |
| WO 94/17304 | 8/1994 | WIPO | F04B 17/00 |

*Primary Examiner*—A. Michael Chambers
*Attorney, Agent, or Firm*—Harold R. Patton; Peter Forrest

[57] ABSTRACT

A biological fluid transport device comprises a cutwater at the junction of at least two blood flow paths. The cutwater is substantially straight, substantially vertical, or both. At least one of the fluid paths may be tubular, and in some embodiments all of the fluid paths are tubular. The shear sensitive fluid may be, without limitation, blood, blood-based combinations, cell culture media, cell suspensions, proteins, and microcapsule suspensions. The device may be part of an extracorporeal circuit (e.g., blood during heart-lung bypass procedures or blood processing), but it need not be. Preferred embodiments of the device include, without limitation, kinetic pumps, mass transfer devices, filters, reservoirs, and heat exchangers.

7 Claims, 6 Drawing Sheets

JUNCTION FOR SHEAR SENSITIVE BIOLOGICAL FLUID PATHS

BACKGROUND

Shear sensitive fluids, including biological fluids such as blood and blood-based combinations, should not be exposed to sudden or extreme changes in pressure or temperature, impacts, vibration, or rapid changes in direction of flow. Nonturbulent flow is the preferred mode of handling shear sensitive fluids.

DISCLOSURE OF THE INVENTION

The invention is a biological fluid transport device comprising a cutwater at the junction of at least two fluid paths or circuits, the cutwater being substantially straight, or substantially vertical, or both. The junction is the location where a fluid path is split into two or more paths. For example, the junction can be an outlet for fluid to leave a device or an inlet for fluid to enter a device. At least one of the fluid paths or circuits may be tubular, and in some embodiments all of the fluid paths or circuits are tubular. The shear sensitive fluid may be, without limitation, blood, blood-based combinations such as "platelet gel," cell culture media, cell suspensions, proteins, and microcapsule suspensions. The device may be part of an extracorporeal bypass circuit but it need not be. Preferred embodiments of the device include, without limitation, kinetic pumps, mass transfer devices, filters, reservoirs, heat exchangers, and blood processing systems (such as diagnostic hemostasis management systems and blood coagulation testing systems).

DETAILED DESCRIPTION

Many biological fluids are shear sensitive. Examples include blood, blood-based combinations, cell culture media, cell suspensions, proteins, and microcapsule suspensions. Any feature, or other obstruction present in the fluid flow path or circuit, can induce high shear by creating a high gradient, that is, a large change in velocity over a small area. (A fluid path is any series of locations occupied by the fluid. A circuit is a path which forms at least a portion of a closed loop, such as would be established with a path from a source of fluid to a device, and another path from the device back to the source. Of course, multiple devices could be employed.)

Practical applications nearly always require that some or all of the fluid change direction so that it can be processed. Thus, most fluid transport devices comprise housings and other components which present junctions at which the fluid may flow in more than one direction. Similarly, such devices may comprise obstructions, interfaces, edges, and the like, somewhere along the path or circuit traveled by the fluid. Between such devices, junctions in fluid tubing and tubing-based accessories may also create undesirable shear stress in the fluids they carry. Examples of such junctions are in-line splitters and connectors which have more than one connection upstream and/or downstream of the flow path through the device; "Y" adapters and "T" adapters; manifolds, and the like.

For example, in extracorporeal bypass circuits, a bodily fluid is removed from the body, presented to special purpose components, and returned to the body. A common extracorporeal circuit includes devices such as kinetic pumps, mass transfer devices, filters, reservoirs, and heat exchangers. (Some of these components may be incorporated into the design of other of the components. For example, a mass transfer device may have an integral heat exchanger, reservoir, filter, or a combination of any or all of them.) In the case of an extracorporeal blood circuit suitable for heart-lung bypass surgery and/or blood processing systems and diagnostic hemostasis management systems, the components may include bubble and membrane oxygenators, arterial filters, cardiotomy reservoirs, bubble separators, blood heat exchangers, and red blood cell washers. Other types of blood management systems employ extracorporeal blood circuits. The invention is suitable for all of these devices, both when they are incorporated into an extracorporeal bypass circuit, and when such devices are used for biological shear sensitive fluids outside the context of extracorporeal bypass (e.g., blood in coagulation testing systems, cell culture media, cell suspensions, proteins, and microcapsule suspensions).

Figure 1:
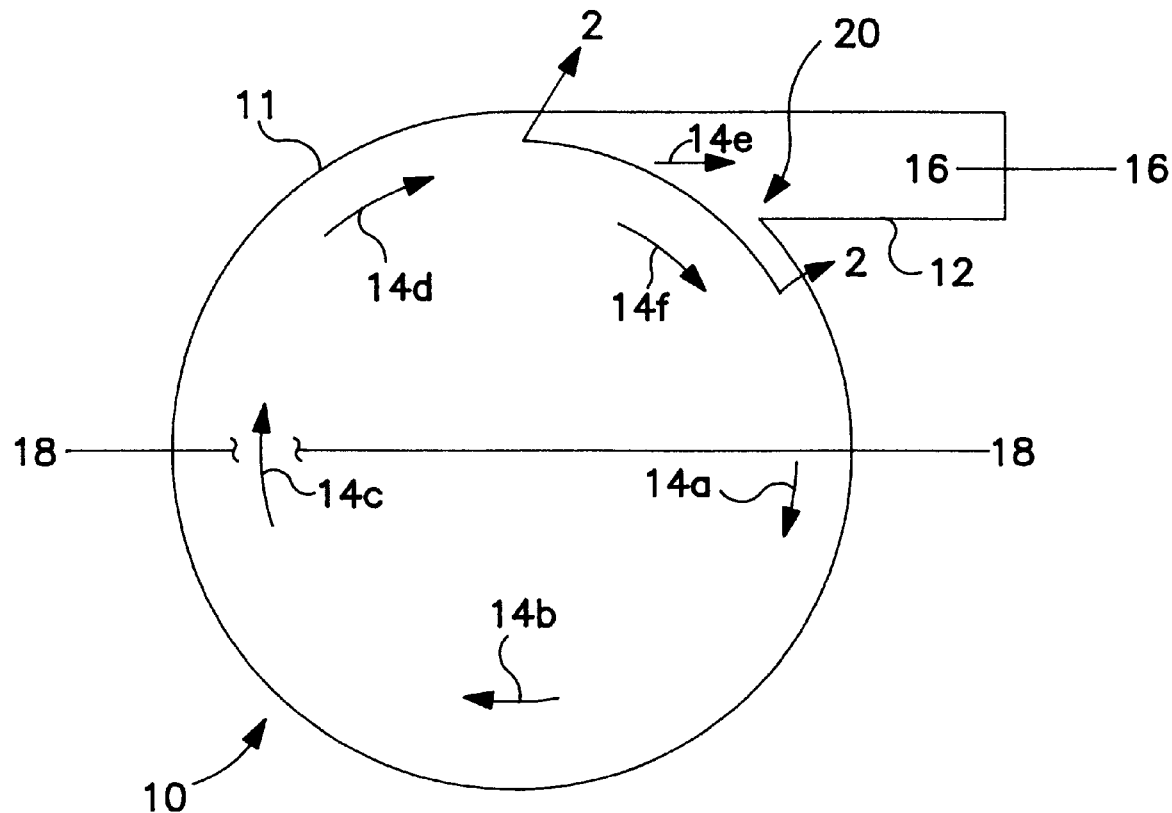
FIG. 1 is a cross sectional schematic view of one embodiment of the invention.

FIG. 1 is a cross sectional schematic view of a common feature in a generic device 10 which, for purposes of illustration only, is generally circular in cross section and has a housing 11 of negligible thickness. The device includes an outlet 12 that permits some or all of the fluid (not shown) to leave the housing when the fluid is traveling in the general direction indicated by flow arrows 14a–14d. The outlet 12 is commonly tubular (for reasons not critical to the invention) and called a "tangential outlet" since the axis of symmetry 16—16 of the outlet 12 does not generally coincide with a diameter 18—18 of the generally circular housing parallel to the flow through the tubular path 12.

Although not shown in FIG. 1, the tangential outlet 12 need not be located so that the flow path axis 16 is exactly tangential with the generally circular cross-sectional profile of the housing. A relatively small amount of offset toward or away from the axis of symmetry 18 of the housing 11 is possible. Similarly, the outlet flow axis 16 and the housing diameter 18 are commonly parallel in the cross-sectional plane, but slight deviations on the order of one to thirty degrees are possible. Finally, the outlet flow axis 16 and the housing diameter 18 are commonly coplanar in the cross-sectional plane, even if not exactly parallel in that plane, but slight deviations on the order of one to thirty degrees are also possible. In any of these three cases, or in any combination of two or three of the cases, minor modifications to the geometry of the invention may be preferred to produce an embodiment of the invention suitable for the particular device under consideration. In all such cases, the principles of the invention would still be employed and therefore all such embodiments are considered to be within the scope of the invention as it is explained below.

Also, a common design technique is to introduce "draft," i.e., small deviations in various dimensions and/or angles, to provide adequate clearance for a molded housing to be removed from its mold. Such deviations are not necessarily reflected in the Figures or this description; however, incorporation of draft or other similar manufacturing techniques into a particular embodiment of the invention is preferred and not considered to be a departure from the scope of the invention.

Generally speaking, fluid flows along the general direction of the flow paths 14a, 14b, 14c and 14d. Fluid then either enters the outlet 12 by following flow path 14e, or remains within device 10 by following flow path 14f. In detail, fluid flow in the vicinity of the junction of the generally circular main portion of the housing 11 and the outlet 12 will be drawn or split, and thus experience shear, at or in the immediate vicinity of the junction of the main housing 11 and the outlet 12. This junction comprises an edge commonly known as cutwater 20. The rate of change of fluid velocity at the cutwater 20 is a source of shear stress in kinetic pumps.

Figure 2A:
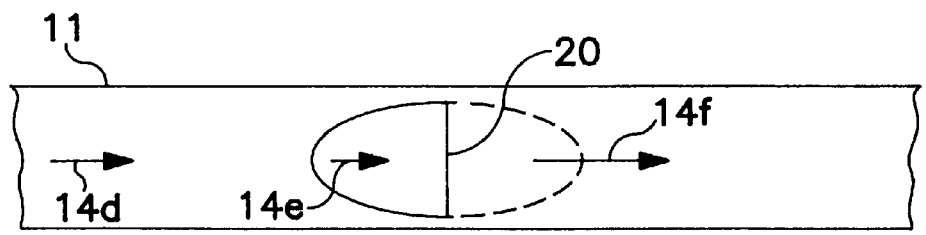
FIG. 2A is a partial cross sectional view of the embodiment of FIG. 1 taken along the line 2—2.
Figure 2B:
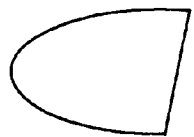
FIGS. 2B through 2O are variations on the view of FIG. 2A.
Figure 2C:
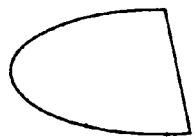
Figure 2D:
Figure 2E:
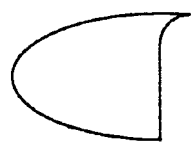
Figure 2F:
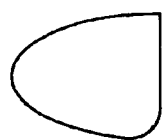
Figure 2G:
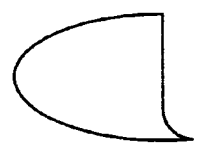
Figure 2H:
Figure 2I:
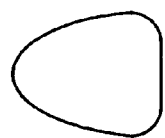
Figure 2J:
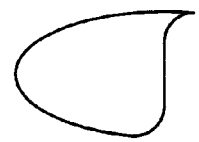
Figure 2K:
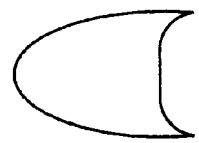
Figure 2L:
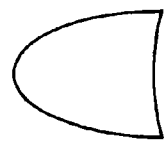
Figure 2M:
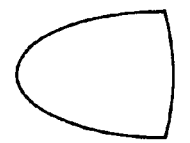
Figure 2N:
Figure 2O:

FIG. 2A is a partial cross sectional view of the cutwater 20 showing together the straight and vertical edge characteristic of the invention, although the edge could be either straight or vertical. The vertical direction is substantially perpendicular to the primary direction of fluid flow at the cutwater location. The edge is designated "straight" or "vertical" to distinguish it from the conventional edge, indicated in phantom, which can appear straight and vertical when viewed directly in the plane of FIG. 1. The conventional edge is shown in phantom as the half-elliptical shape that follows naturally if outlet 12 is a right circular cylinder, as is conventional, and intersects circular housing 11 along a generally tangential path. In the context of the invention, a "straight" cutwater or a "vertical" cutwater can have minor deviations from a perfectly straight and/or perfectly vertical linear edge, as long as those deviations are not significant on the scale of the vertical length (height) of the cutwater. For example, the cutwater could be straight or linear from end to end, but slanted slightly from vertical as shown in FIGS. 2B and 2C. FIGS. 2D through 2K show cutwaters which have minor curves at upper (FIGS. 2D and 2E) or lower (FIGS. 2F and 2G) points, or both (FIGS. 2H, 2I, 2J, and 2K). A slight curvature could be present over substantially all of the cutwater, as shown in FIGS. 2L and 2M. The cutwater could have more than one linear segment, as shown in FIGS. 2N and 2O, with a slight angle between the segments. The apex of the angle need not be equidistant from the upper and lower points of the cutwater. Combinations of all of the above configurations are also possible. In all cases, the cutwater is considered to be substantially straight or substantially vertical or substantially straight and vertical, depending on the exact configuration chosen.

Although the above description assumes that fluid within the device 10 leaves the housing 11 through the outlet 12, the invention could also be practiced in a device in which the fluid direction was reversed. In such an embodiment, fluid would enter through a tangential inlet, pass a junction comprising a cutwater shaped as described above, and enter the device. Thus, in the broadest sense, the invention is a device for carrying biological shear sensitive fluids, comprising a straight or vertical cutwater at a junction of at least two fluid paths or circuits within the device. The junction is the location where the fluid flow within a fluid path is split into two or more other paths.

Shear stress is the most significant contributor to hemolysis in blood pumps. FIGS. 3 and 4A to 4E illustrate an embodiment of the invention for use on an otherwise conventional centrifugal blood pump. In general, such a device comprises a housing 100 having an inlet (not shown) for fluid (not shown) entering the housing 100, and a tangential outlet 110 for the fluid to exit the housing 100. Within the housing 100, a rotating impeller increases the angular velocity of the fluid, but the impeller design preferably minimizes shear on the fluid. Once the fluid reaches the junction between the housing and the tangential outlet, it is exposed to the cutwater as described above. An example of such a pump is the BioPump model BP-80 commercially available from Medtronic Bio-Medicus of Minneapolis, Minn., USA.

Figure 4E:
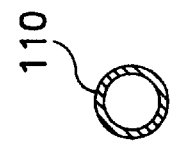
FIGS. 4A through 4E are partial cross sectional views of the embodiment of FIG. 3 taken along the lines 4A—4A to 4E—4E, respectively.
Figure 4D:
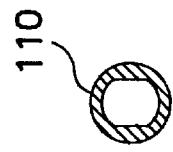
Figure 4C:
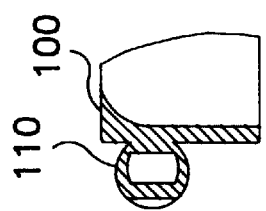
Figure 4B:
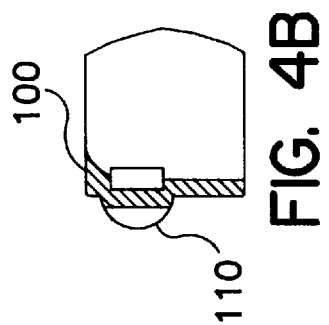
Figure 4A:
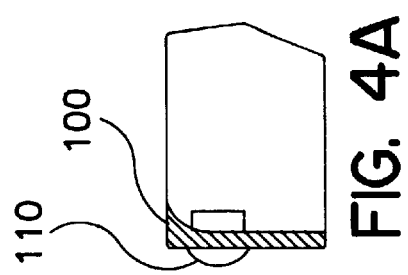

FIG. 4A shows a straight and vertical cutwater 120. FIG. 4B shows that the cross sectional profile of fluid outlet 110 is preferably rectangular (neglecting slight deviations due to draft) at a location common to the volume of the main portion of housing 100 and outlet 110. This cross sectional profile gradually tapers, as seen from the sequential cross sectional views of FIGS. 4C and 4D. FIG. 4E shows that the tapering does not continue to the end of the outlet where the fluid exits the pump; that is, the inner diameter of fluid outlet 110 is generally circular when viewed in cross section at fluid outlet 110. The tapering is a preferred embodiment that is not necessary to the practice of the invention. Also, the cross sectional area of the outlet 110 at the exit of the pump (FIG. 4E) is preferably greater than the cross sectional area of the outlet 110 at the junction with the main portion of the housing 100. This is to accommodate the inner diameter of tubing typically connected to the pump at the outlet, but it is not necessary to the practice of the invention.

Figure 4F:
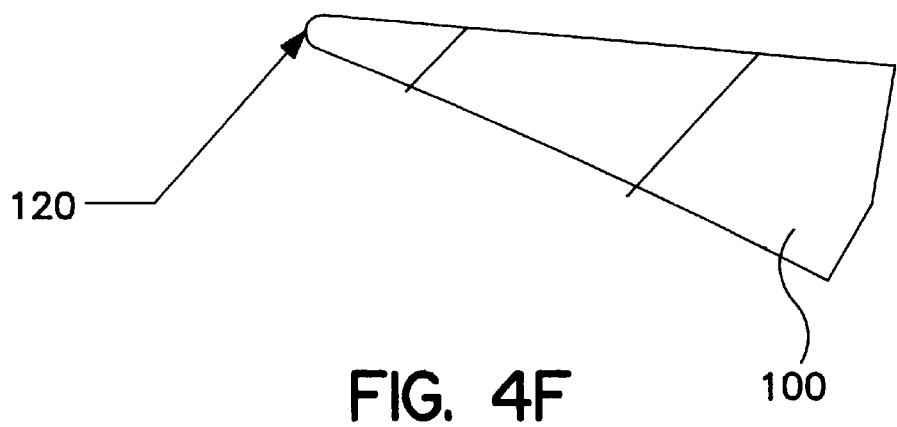
FIG. 4F is a close up view of the portion of FIG. 3 within the circle designated 4F.

While cutwater 120 reduces shear stress due to its vertical and/or straight configuration alone, it is preferred to radius the edge. As shown in detail in FIG. 4F, cutwater 120 has a radius of curvature in the horizontal plane of preferably 0.001 to 0.030 inch, and most preferably at least 0.004 inch. The choice of radius of curvature should take into account the clearance between the cutwater and the impeller.

The housing 100 may be constructed according to conventional techniques from a variety of materials approved for contact with biological fluids, such as medical grade polycarbonates suitable for blood and blood-based mixtures. A preferred material is available from the Bayer Corporation or the General Polymers Division of the Ashland Corporation under the Bayer tradename MAKROLON, specifically type RX-2530-1118 (see http://www.ashchem.com/GP/data/1373.htm). The surface finish on surfaces of the housing 100 which contact blood is preferably SPI/SPE No. 2. Rough surfaces, scratches, scuffs, nicks, cracks, etc. should be eliminated to reduce shear stress in the fluid. The inner surface can be coated with an antithrombogenic agent not essential to the invention.

Figure 5:
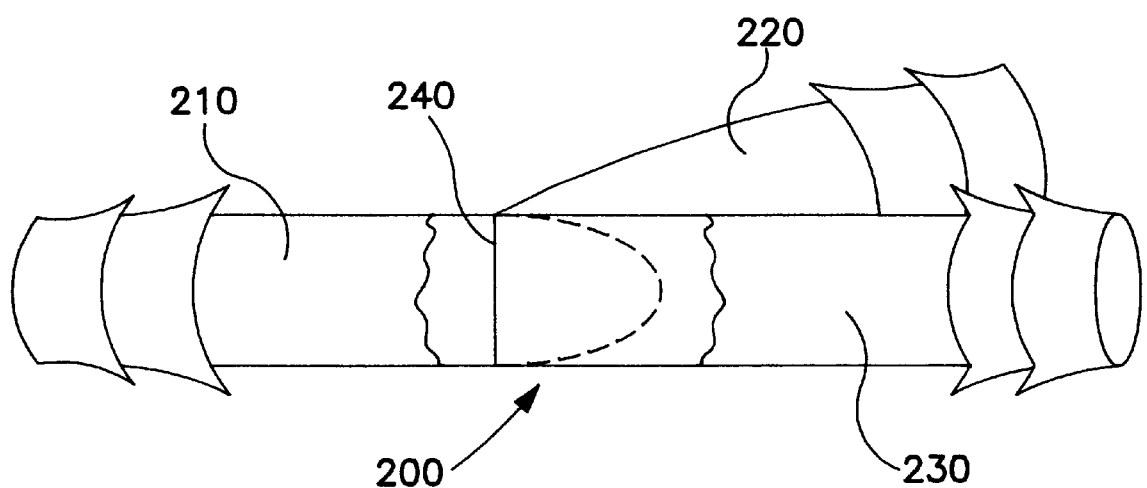
FIG. 5 is a perspective view, including a cutaway portion, of an embodiment of the invention.

FIG. 5 shows a "2-way" connector 200 comprising a first fluid path 210 and second and third fluid paths 220 and 230. The first fluid path 210 can be an inlet to connector 200, with the second and third fluid paths 220 and 230 being outlets. A substantially straight and/or vertical cutwater 240 is shown in the cutaway portion at the junction of the three fluid paths circuits. Again, the conventional elliptical cutwater is shown in phantom. This could be an in-line flow connector for an otherwise conventional connection to suitable tubing, or it could be the configuration of an inlet or outlet on another otherwise conventional device (not shown), such as a mass transfer device (such as a bubble or membrane oxygenator), filters (such as an arterial or cardiotomy filter), reservoirs (such as a blood or cardiotomy reservoir), and heat exchangers. The embodiment of FIG. 5 is suitable for extracorporeal bypass circuit components, as well as components and circuits used for biological shear sensitive fluids outside the context of extracorporeal bypass (e.g., cell culture media, cell suspensions, proteins, and microcapsule suspensions). Application of the substantially straight or substantially vertical cutwater to "3-way" connectors, manifolds, and the like can easily be accomplished.

The success of the invention is believed to be due to reduction of elevated shear forces in the vicinity of the cutwater created by a vortex set up by the flow over the cutwater surface. Fluid approaching a curved cutwater on the fluid outlet side follows a partially upward path as it crosses over the cutwater back to the main chamber of the device. This movement results in a mean rotational motion, that is, a vortex. Fluid upstream of the cutwater and on the bottom portion of the vortex, that would otherwise move to the main chamber of the device, is forced to move to the fluid outlet side of the cutwater in a turbulent motion. Turbulent motion is undesirable since it creates rapidly changing velocity components that induce shear stress on the fluid. The inventive cutwater induces less shear stress because it reduces rate of change of velocity components on either side of the cutwater. The conventional geometry induces higher shear by generating higher levels of vorticity as compared to the invention. Vorticity is generated as the fluid passes the cutwater. These vortices create substantial changes in the magnitude and direction of the fluid (i.e. change in velocity components) over a given area. The inventive geometry reduces induced rotational forces on the fluid and consequently reduces the compression of the fluid path.

EXAMPLES

Blood trauma caused by centrifugal pumps was measured for two sets of pumps which varied only in the cutwater configuration in a conventional tangential outlet. The configuration illustrated in FIGS. 2 through 4 above was compared to a control group, that is, a comparative example which differed only in the design of the cutwater. The comparative example had a cutwater identical to that of a standard commercial-grade centrifugal blood pump designated Model Number BP80, available from Medtronic Bio-Medicus, Inc. of Minneapolis, Minn., USA.

The in-vitro hemolysis test measured blood trauma caused by the extracorporeal centrifugal pumps. Plasma free hemoglobin levels are measured and reported over a four hour test duration. Free hemoglobin generation rate (mg/dl/hour) is calculated. Hematocrit is adjusted at the start of the test and monitored throughout the four hour test duration.

The test requires 1000 cc of fresh bovine blood less than eight hours old. The blood is preferably washed and resuspended in saline, but this is not required. The blood plasma had an initial plasma free hemoglobin level less than 25 mg/dl. The blood did not "auto" hemolyze. The following test conditions were applied:

| | |
|---|---|
| Blood Flow Rate | 4 liters/min ± 5% |
| Differential Pressure ($P_{out} - P_{in}$) | 400 mm Hg ± 20 mmHg |
| Temperature | 37 C. ± 1 C. |
| Blood Volume | 1000 cc ± 100 cc |
| Hematocrit | 30% ± 1% adjusted with saline solution |

The maximum plasma free hemoglobin increase of the control from the baseline sample should be 10 mg/dl (milligrams per deciliter). If the negative control does not meet this criteria, the test for the device hemolysis is rendered invalid. Each device is tested over four hours, flowing at 4 l/minute.

Plasma free hemoglobin (mg/dL) is measured at time 0 and at 60 minute intervals. Hematocrit is measured at time 0. Hematocrit is typically not expected to change substantially in these in-vitro tests. Flow (Liters/min), temperature, and pressure are measured throughout the test.

The test requires a kinetic pump, a pressure monitoring device, a flow probe, a temperature monitoring device, a microhematocrit centrifuge, a blood bank centrifuge, a sequence of pressure reducers, a spectral photometer, sodium chloride 0.9%, sterile, for adjusting hematocrit and anticoagulant. The design, number, and location of the pressure reducers are selected to minimize introduction of additional hemolysis. For example, a series of four inline reducers in the pump outlet line is preferred.

The fluid handling circuit is a closed system, including the kinetic pump, a blood reservoir bag, 4 to 5 feet of PVC tubing (⅜ inch I.D.) and plastic connectors. Hematocrit of the blood is adjusted to 30% by adding saline. Blood samples are drawn for blood trauma analysis according to the sampling plan.

Figure 3:
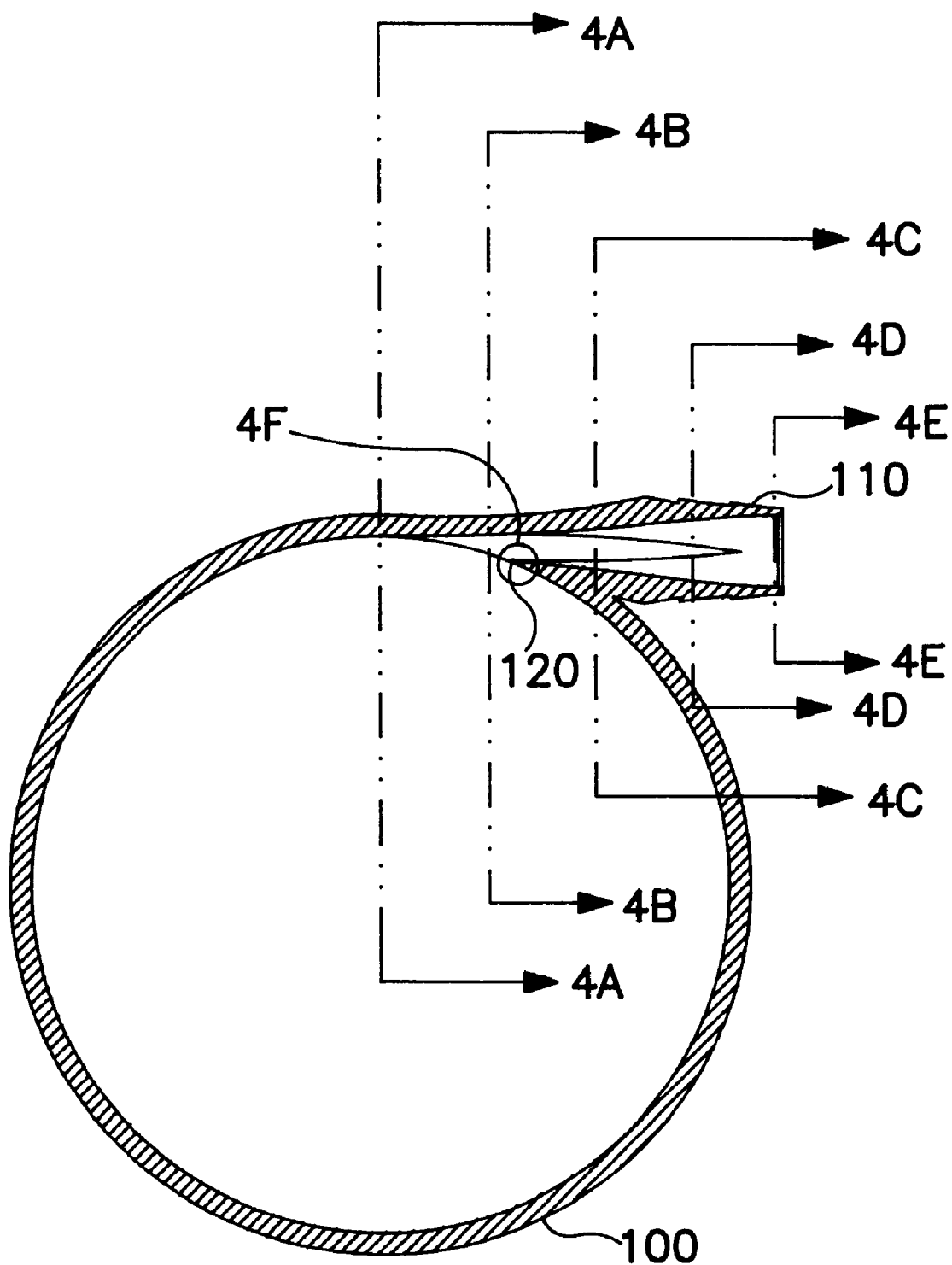
FIG. 3 is cross sectional view of a preferred kinetic blood pump embodiment of the invention.

The absolute rate of hemolysis was measured for 48 samples of a kinetic pump using a housing having the configuration of FIGS. 3–4. The absolute hemolysis rates are listed in the second column of Table 1. The third column of Table 1 shows the ratio of the hemolysis rates of the pumps of FIGS. 3–4 to the comparative example, pumps having the cutwater identical to that of the commercially available BP-80 pump as described earlier. Entries of 1.00 indicate no change in hemolysis rate, with entries less than 1.00 indicating improvement and entries greater than 1.00 indicating degradation in performance. Sample number 1 was omitted from the data analysis.

Figure 6:
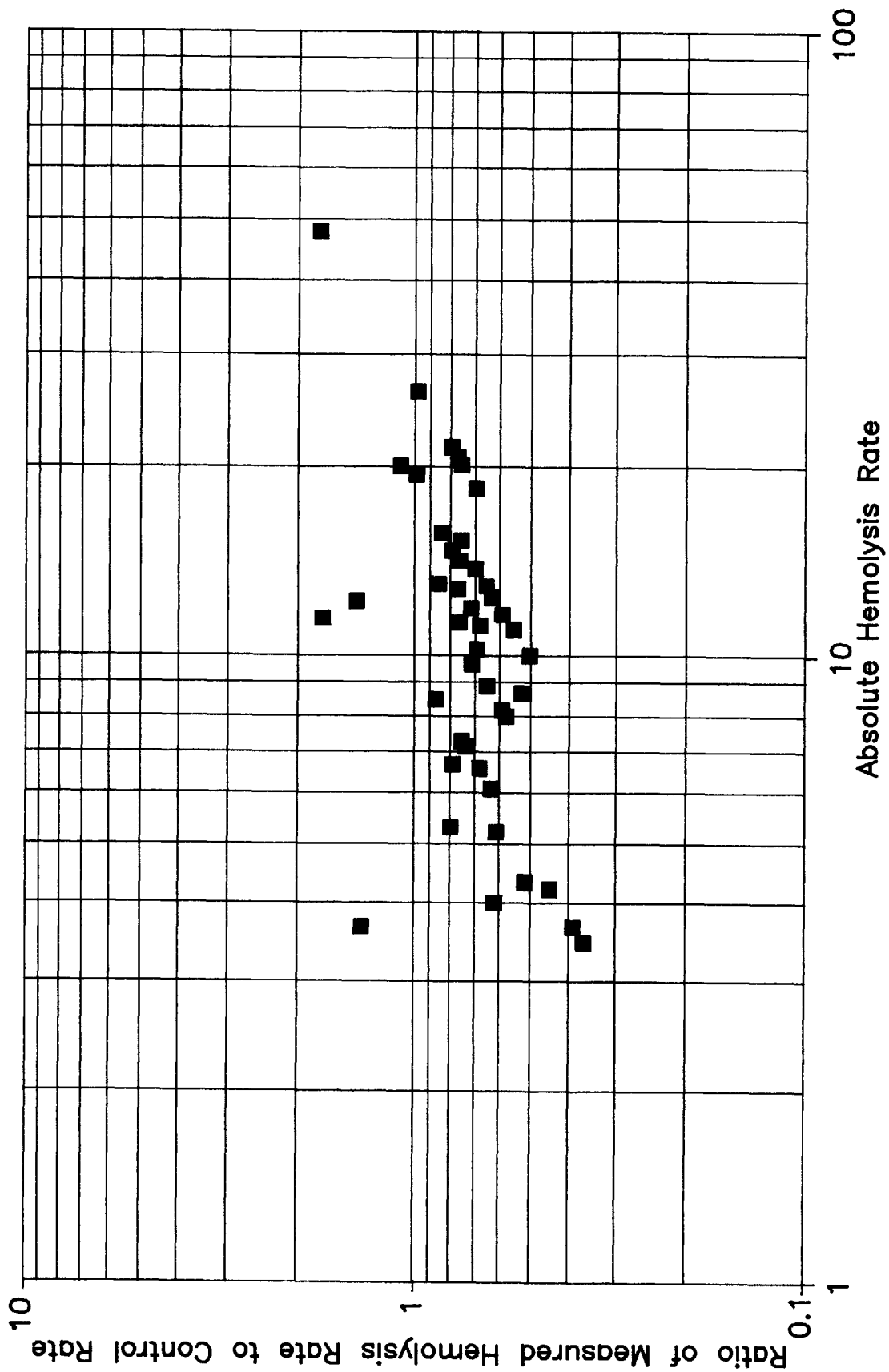
FIG. 6 is a log-log scatter plot of the data of Table 1.

As indicated in the mean (N=47) hemolysis ratios, the improved cutwater design resulted in a 22% decrease in rate of hemolysis. As shown in FIG. 6, the decrease in hemolysis was present in the vast majority of cases over a range of absolute hemolysis rates from approximately 3 to 20.

TABLE 1

| Sample | Absolute Rate | Hemolysis |
|---|---|---|
| 1 | 93.19* | 3.53* |
| 2 | 26.48 | 1.00 |
| 3 | 47.65 | 1.81 |
| 4 | 20.37 | 0.77 |
| 5 | 7.339 | 0.76 |
| 6 | 6.164 | 0.64 |
| 7 | 6.645 | 0.69 |
| 8 | 8.578 | 0.89 |
| 9 | 13.103 | 0.87 |
| 10 | 11.519 | 0.76 |
| 11 | 10.374 | 0.69 |
| 12 | 13.188 | 0.87 |
| 13 | 5.346 | 0.81 |
| 14 | 11.487 | 1.75 |
| 15 | 4.074 | 0.62 |
| 16 | 4.042 | 0.62 |
| 17 | 4.264 | 0.45 |
| 18 | 7.171 | 0.75 |
| 19 | 3.507 | 0.37 |
| 20 | 3.698 | 0.39 |
| 21 | 26.45 | 0.99 |
| 22 | 21.704 | 0.81 |
| 23 | 20.895 | 0.78 |
| 24 | 18.657 | 0.70 |
| 25 | 11.329 | 0.69 |

TABLE 1-continued

| Sample | Absolute Rate | Hemolysis |
|---|---|---|
| 26 | 12.936 | 0.79 |
| 27 | 12.022 | 0.73 |
| 28 | 8.789 | 0.54 |
| 29 | 11.729 | 0.60 |
| 30 | 10.081 | 0.51 |
| 31 | 12.497 | 0.64 |
| 32 | 19.783 | 1.01 |
| 33 | 12.286 | 1.45 |
| 34 | 5.271 | 0.62 |
| 35 | 6.783 | 0.80 |
| 36 | 4.367 | 0.52 |
| 37 | 8.99 | 0.66 |
| 38 | 8.044 | 0.59 |
| 39 | 9.757 | 0.71 |
| 40 | 8.244 | 0.60 |
| 41 | 13.042 | 0.66 |
| 42 | 11.088 | 0.56 |
| 43 | 15.33 | 0.78 |
| 44 | 13.891 | 0.71 |
| 45 | 14.289 | 0.78 |
| 46 | 14.784 | 0.81 |
| 47 | 20.306 | 1.11 |
| 48 | 15.699 | 0.86 |
| Count | 47 | 47 |
| Mean | 12.43 | 0.78 |
| Std. Deviation | 7.84 | 0.28 |

*indicates data not used to calculate mean and standard deviation

We claim:

1. A centrifugal pump for biological shear sensitive fluids, comprising, in combination:
   (a) a housing having an inlet and a cylindrical portion defining a first fluid path of constant radius;
   (b) an outlet connected to the housing and defining a second fluid path that tangentially connects to the first fluid path and has a changing cross-sectional profile as the second fluid path proceeds away from the housing;
   (c) a substantially vertical cutwater at a junction of the first and second fluid paths;
   (d) within the housing, a rotating impeller designed to propel the fluid from the first fluid path toward the cutwater such that fluid flows either into the second fluid path or remains in the first fluid path.

2. A centrifugal pump for biological shear sensitive fluids, comprising, in combination:
   (a) a housing having an inlet and a cylindrical portion defining a first fluid path of constant radius;
   (b) an outlet connected to the housing and defining a second fluid path that tangentially connects to the first fluid path and has a changing cross-sectional profile as the second fluid path proceeds away from the housing;
   (c) a substantially straight cutwater at a junction of the first and second fluid paths;
   (d) within the housing, a rotating impeller designed to propel the fluid from the first fluid path toward the cutwater such that fluid flows either into the second fluid path or remains in the first fluid path.

3. The centrifugal pump of claim 1 or 2 in which the cutwater is both substantially straight and substantially vertical.

4. The device of claim 1 or 2 in which at least one of the fluid paths is an inlet for fluid to enter at least one other path.

5. The centrifugal pump of claim 1 or 2 in which the shear sensitive fluid comprises a fluid chosen from the group consisting essentially of blood, cell culture media, cell suspensions, proteins, and microcapsule suspensions.

6. The centrifugal pump of claim 1 or 2 in which the cutwater has a horizontal radius of curvature of between 0.001 to 0.030 inch.

7. The centrifugal pump of claim 2 in which the cutwater has a horizontal radius of curvature of at least 0.004 inch.

* * * * *